United States Patent [19]

Haagensen et al.

[11] Patent Number: 5,213,830
[45] Date of Patent: May 25, 1993

[54] METHOD OF DETECTING WORMS IN MEAT

[75] Inventors: Peter Haagensen, Valby; Alicia de Francisco, Hvidovre; Lars Munck, Helsingor, all of Denmark

[73] Assignee: Lumetech, Hellerup, Denmark

[21] Appl. No.: 488,070

[22] PCT Filed: Oct. 19, 1989

[86] PCT No.: PCT/SE89/00578
§ 371 Date: Jun. 19, 1990
§ 102(e) Date: Jun. 19, 1990

[87] PCT Pub. No.: WO90/04782
PCT Pub. Date: May 3, 1990

[30] Foreign Application Priority Data

Oct. 19, 1988 [SE] Sweden .................... 8803724-7

[51] Int. Cl.[5] ................... G01N 21/00; G01N 21/17; G01N 21/62
[52] U.S. Cl. ................... 426/237; 250/338.1; 356/51; 356/432
[58] Field of Search ........ 426/237, 241, 248, 231; 250/372, 338.1; 356/432, 51; 435/173, 29

[56] References Cited

U.S. PATENT DOCUMENTS

| | | | |
|---|---|---|---|
| 3,918,818 | 11/1975 | Giles | 356/239 |
| 4,061,788 | 12/1977 | Wommack | 426/248 |
| 4,226,540 | 10/1980 | Barten et al. | 356/445 |
| 4,631,413 | 12/1986 | Jensen et al. | 250/458.1 |
| 4,744,131 | 10/1987 | Hartmann | 452/198 |

OTHER PUBLICATIONS

Article: "Use of Ultraviolet Light to find Parasitic Nematodes in situ", by John C. Pippy, *Fisheries Research Board of Canada*, vol. 27, No. 5 (1970).
Derwent World Patents Abstract No. 86-008149/02 European Patent 174012.
Waag DE3205394-Dialog Assess. #3251663 WPI Acc. No. 83-747893/35 XRPX Acc No. N83-151250.

*Primary Examiner*—Margaret Moskowitz
*Assistant Examiner*—Lori L. Yuan
*Attorney, Agent, or Firm*—Merchant, Gould, Smith, Edell, Welter & Schmidt

[57] ABSTRACT

Method for quality control of meat products, especially fish flesh, with regard to the presence of worms. The product to be subjected to quality control, or a sample thereof, is exposed to electromagnetic radiation within the range of about 800–1800 nm, and the irradiation transmitted through said product or sample as a result of this irradiation, is analyzed for identification of characteristic absorption by worms in said product or sample.

2 Claims, 1 Drawing Sheet

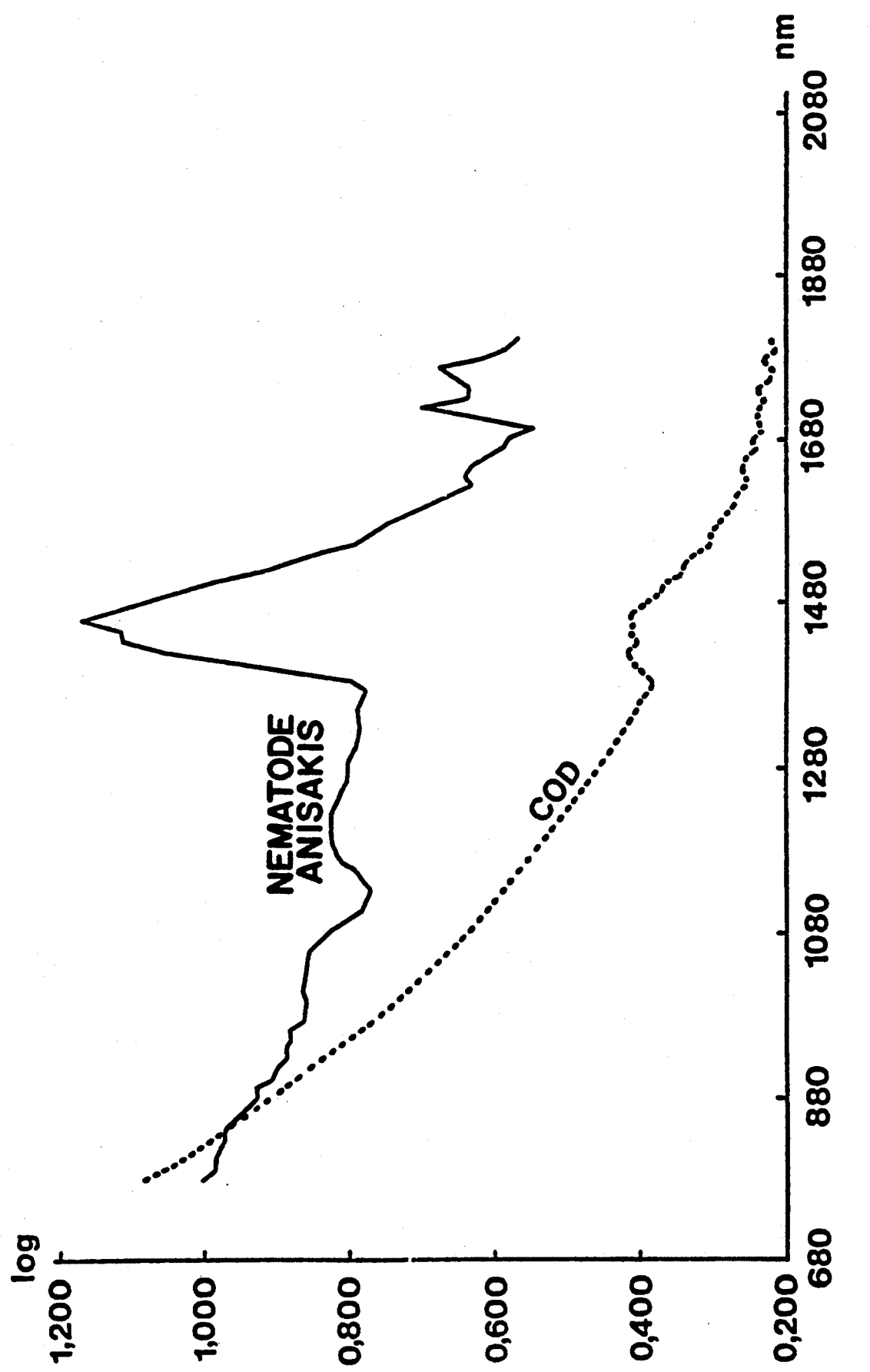

METHOD OF DETECTING WORMS IN MEAT

It is common knowledge that worms in meat make it unfit for foods; several species even cause fatal poisonings or diseases. Consequently, one tries to detect the presence of worms in meat so as to be able to determine the meat quality. Many worms are transparent and therefore difficult to detect with the naked eye and even with a microscope. This is the case with, for example, several worm species parasitising on fish.

Journal Fisheries Research Board of Canada, Vol. 27, No. 5, 1970 reports that a number of parasitic nematodes are detectable in fish since they autofluoresce when irradiated by UV light.

However, this detection method implies that the fish flesh has been frozen before irradiation. This involves disadvantages, since the freezing action requires additional time and costs and since one often wants to sell the fish in the fresh state.

According to the invention, it has now surprisingly been discovered that these disadvantages are obviated in a worm detection method which uses, instead of UV light, IR light by means of which the meat product/the sample thereof is irradiated for detection of worms.

FIG. 1 shows an IR spectrum (transmission) recorded according to the invention, of the nematode Anisakis (living) and fresh cod flesh, respectively, within a wavelength range of 800–1800 nm. The spectrum was recorded by means of a Zeiss UMSP80 type Universal Microspectrophotometer. As appears from the spectrum, Anisakis can be clearly distinguished from cod flesh in large areas of the wavelength range involved and suitably in the range of about 1100–1700 nm, preferably about 1700 nm or 1300 nm to evade the absorption maximum (1480 nm) of any water present.

Similar spectra are obtained with dead Anisakis as well as living and dead Phocanema.

A system for automatic fish fillet control as defined in EP 0,128,889, can be modified for automatic meat control with regard to the presence of worms. This modification implies that the UV source and the fluorescence detector are replaced by an IR source and an IR detector (which can also be a TV camera), which are arranged above and, respectively, below, the conveyor belt which in this case is IR permeable.

We claim:

1. A method for performing quality control inspection of fresh cod flesh wherein the presence of nematode Anisakis and Phocanema is detected, comprising:
    exposing at least part of the fresh cod flesh to electromagnetic radiation within the range of approximately 800–1800 nm from an electromagnetic radiation source;
    receiving said electromagnetic radiation transmitted through said fresh cod flesh in a detector; and
    analyzing said received electromagnetic radiation for identification of absorption characteristics of the nematode Anisakis and Phocanema.

2. The quality control method of claim 1, wherein said range of electromagnetic radiation is approximately 1100–1700 nm.

* * * * *